Figure 1:
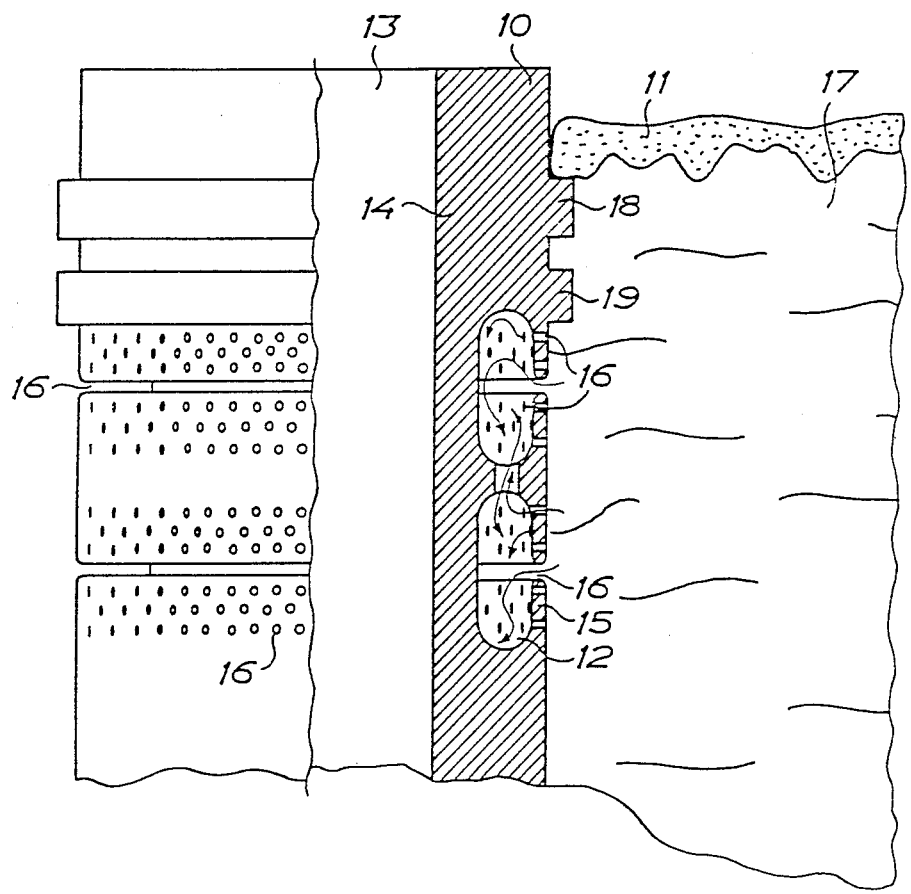

United States Patent [19]

Lundgren

[11] Patent Number: 4,752,294
[45] Date of Patent: Jun. 21, 1988

[54] ELEMENT FOR CONTROLLED GROWTH INTO SURGICALLY INTERVENED AREAS

[76] Inventor: Dan Lundgren, Kyrkvägen 5, S-430 80 Hovås, Sweden

[21] Appl. No.: 885,591
[22] PCT Filed: Feb. 26, 1985
[86] PCT No.: PCT/SE85/00091
§ 371 Date: Jul. 7, 1986
§ 102(e) Date: Jul. 7, 1986
[87] PCT Pub. No.: WO86/02824
PCT Pub. Date: May 22, 1986

[30] Foreign Application Priority Data

Nov. 7, 1984 [SE] Sweden ................................ 8405568

[51] Int. Cl.$^4$ .............................................. A61F 2/02
[52] U.S. Cl. .......................................... 623/11; 623/66; 623/16; 427/2
[58] Field of Search ............... 623/1, 2, 11, 16, 66; 604/175; 128/334 R, 335.5; 427/2

[56] References Cited

U.S. PATENT DOCUMENTS

| | | | |
|---|---|---|---|
| 3,700,380 | 10/1972 | Kitrilakis | 623/66 |
| 4,061,134 | 12/1977 | Samuels et al. | 623/1 X |
| 4,374,669 | 2/1983 | MacGregor | 427/2 X |
| 4,588,667 | 5/1986 | Jones et al. | 430/128 X |
| 4,608,052 | 8/1986 | Van Kampen et al. | 623/16 X |

FOREIGN PATENT DOCUMENTS

| | | |
|---|---|---|
| 3416471 | 10/1985 | Fed. Rep. of Germany . |
| WO81/02668 | 3/1981 | PCT Int'l Appl. . |
| 75044625-0 | 9/1978 | Sweden . |
| 2005546A | 10/1978 | United Kingdom . |

OTHER PUBLICATIONS

Patent Cooperation Treaty International Preliminary Examination Report for Application PCT/SE85/00091.
International Search Report for Applicant's Corresponding PCT Application, PCT/SE85/00091, Feb. 1985.

*Primary Examiner*—Richard J. Apley
*Assistant Examiner*—Alan W. Cannon
*Attorney, Agent, or Firm*—Merchant, Gould, Smith, Edell, Welter & Schmidt

[57] ABSTRACT

An element for control growth of tissue into surgically intervened areas, e.g. for passages through skin or mucous membrane, or for controlled growth of tissue around surgically treated teeth which have lost part of the supporting tissue thereof, forms one or more undercut cavities (12) which are each available through one or more openings (16) on the outside of the element. The surfaces of the element which are exposed to surrounding tissue consist of or are coated with a biocompatible material.

8 Claims, 2 Drawing Sheets

ELEMENT FOR CONTROLLED GROWTH INTO SURGICALLY INTERVENED AREAS

The invention relates to an element for controlled growth of tissue into surgically intervened areas, e.g. for passages through skin or mucous membrane. An element may be concerned which is used for attaching a prosthesis in the body or which forms per se such a prosthesis. In a modified embodiment, the element can also be utilized for controlled regeneration of supporting tissue around teeth, which has been lost.

When an element is to be incorporated into a tissue or is to be implanted in such a way that it must pass through several tissues as the case is inter alia when a passage has to be made through the skin or through a mucous membrane, it is required that the element is biocompatible, i.e. the element must be accepted by the tissue, and the problem arises to provide a safe retension of the element in the surrounding tissue so that the element will not be dislocated mechanically. An unsatisfactory biocompatibility as well as an insufficient retension causes irritation of the tissues and possible tissue rupture as a consequence thereof in connection with the element. This means that reactive zones of connective tissue with a more or less significant strain of inflammation are formed, which results in the element no longer being maintained harmonically incorporated into the tissue region. The element starts to drift and to lose its function. As far as passages through skin or mucous tissue are concerned, the tissue irritation moreover results in epithelium growing down around the element with repellation as the final consequence thereof. When lost supporting tissue is regenerated around teeth, it is moreover necessary to control in a specific order the growth of the specific tissues which form attachment for the tooth, into the element.

In order to solve these problems the element of the invention has obtained the characteristics appearing from claim 1.

Figure 2:
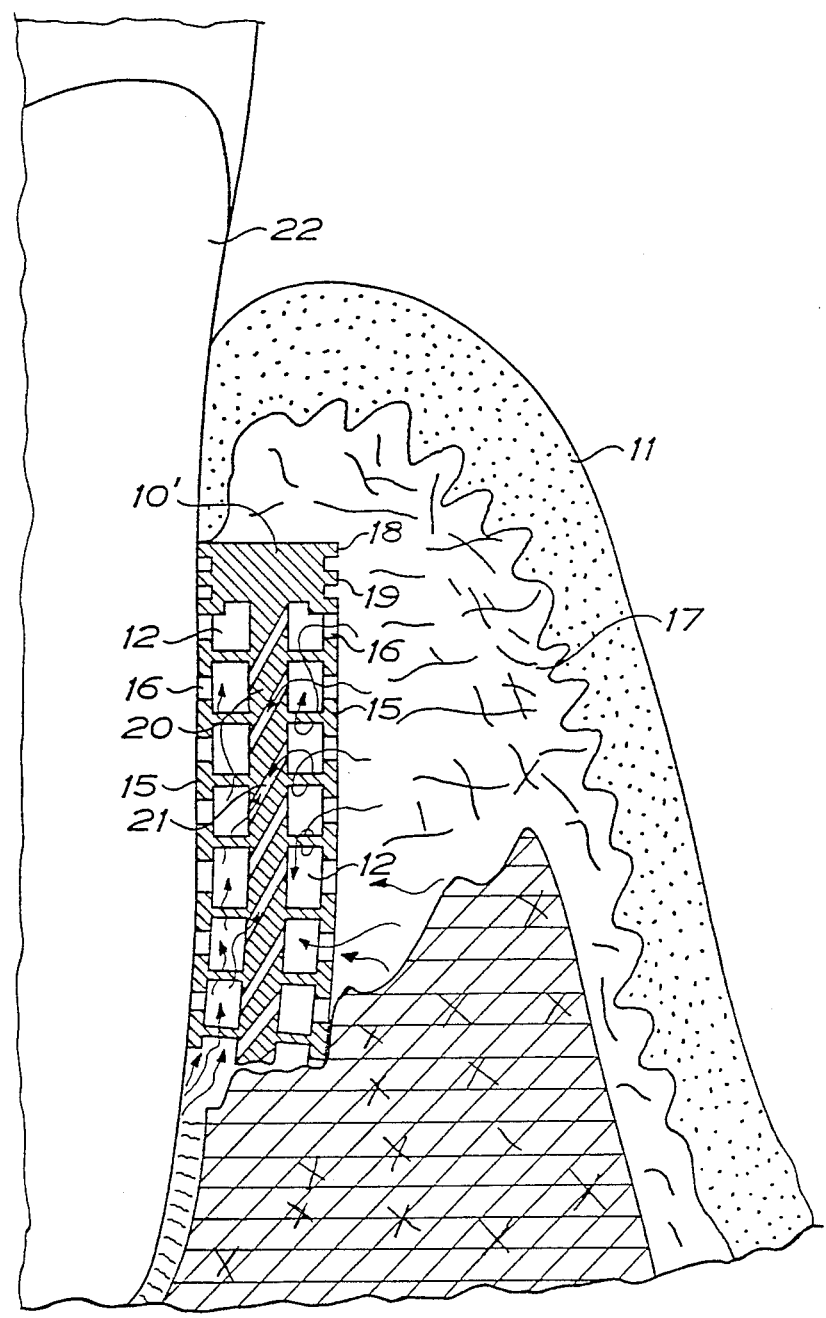

In order to explain the invention in more detail reference is made to the accompanying drawings in which FIG. 1 is a diagrammatic sectional view illustrating an implanted element which extends through the outer skin, and FIG. 2 is a diagrammatic sectional view illustrating a modified element for regeneration of lost supporting tissue around teeth.

In FIG. 1, an implanted element 10 of the invention is shown, which extends through the outer skin the outermost cellular layer, the epithelium, of which is shown at 11.

In the embodiment shown herein, the element is tubular and can comprise e.g. an implanted conduit for performing peritoneal dialysis. The conduit can be rigid or flexible. It forms a number of cavities 12 which are defined towards the passage 13 through the element by a solid wall 14. Towards the outside surface of the element the cavities are defined by a perforated wall 15 the perforations of which are indicated at 15 and comprise circular openings as well as circumferential slots. The connective tissue which is indicated at 17, grows into the cavities 12, matures and attains a structural organization which prevents the epithelium 11 from growing downwards along the surface of the element and from infiltrating the layer of connective tissue adjacent the element and thus preventing the epithelium from enclosing the element 10, which would result in repellation of the element. The growth of the connective tissue into the cavities should be such that the connective tissue inside the cavities will be complete and will be fully matured, i.e. the slots 16 should be sufficiently large so as to allow the cells of the connective tissue as well as the blood vessels necessary for the supply to the connective tissue, to grow into the cavities and thus to create such conditions that the cells of the connective tissue can produce fibers of such tissue and matrix and that the components of the connective tissue can mature and be renewed in a normal way.

Taking these conditions into consideration, it is proposed according to the invention to arrange the openings 16 with a minimum dimension of 30 $\mu$m. The depth of the cavities 12, i.e. the distance between the walls 14 and 15, also should have a minimum size of 30 $\mu$m.

According to the invention, the element 10 on the surfaces which are exposed to the surrounding tissue, comprises a biocompatible material, and an excellent material of this type is titanium. The element in its entirety can consist of titanium, but it is preferred that the element on said surfaces, i.e. on the outside surface thereof, in the openings 16 and in the cavities 12 is coated with titanium by a thin layer thereof being deposited on a supporting body by evaporation in vacuum. This supporting body can be rigid or flexible and can be made e.g. of silicon rubber, polyester, or polytetrafluoro ethylene. In the embodiment shown, openings 16 are formed with sharp edges, but the edges can be made in another way e.g. with a chamfer on the outside surface of the element or inside the cavities 12, or they can be curved.

When an element for passage through skin or mucous membrane is implanted in the body tissue in the manner described, the connective tissue is allowed to mature adjacent the surface of the element and inside the cavities in order to achieve a reliable and permanent retension of the element while the epithelium is prevented from growing down around the element at the passage through the skin or the mucous membrane.

If the element surfaces which are exposed to the surrounding soft tissue, are given a surface topography in the shape of grooves extending in parallel with each other and having a predetermined minimum depth and walls which are so steep that they form significant angles between the bottom of the groove, the walls thereof and the portion between two grooves, the drift of epithelium cells along said surface can be prevented or alternatively greatly retarded in a direction perpendicular to the extension of the grooves when elements forming passages through skin or mucous membrane are implanted.

The region of the element surface immediately above the uppermost opening in the perforated wall of the element, which is exposed to the epithelium layer, therefore is given a suitable profile, and this region e.g. can form circumferential ribs 18 and 19 according to FIG. 1. This arrangement provides a supplementary protection against growth of epithelium downwards along the surface of the element for the period necessary for the granulation tissue of the wound region to mature to a firm structured connective tissue.

When elements adapted for the penetration of skin or mucous membrane in regions requiring a longer healing period so as to provide for the connective tissue sufficient possibilities of maturing, are being implanted, the surgical operation preferably is performed in two stages. Stage 1 is a surgical operation with total implantation of the element including a tube closure, if any, in soft or hard tissue. After a period adjusted individually, stage 2 is performed wherein a desired portion of the element is exposed for connection to a tissue or organ-external system.

When lost supporting tissue around teeth is to be regenerated, a modified element 10' according to FIG. 2 is utilized. This element principally is formed as the wall of the tubular element previously described, but there is the difference that the wall in this case is double with the openings 16 facing two directions. The intermediate wall 20 can be a solid or perforated wall with passages 21 causing retarded growth due to a corrugated labyrinthine course of the cells forming connective tissue and bone, which are more rapidly regenerating than the root membrane cells forming root cement. These passages can also be made more directly penetrating but in that case should be filled with resorptive material so as to retard the growth of the more rapid cells. After an individually adjusted surgical operation the element is put into contact with the root surface 22 which should be made the object of regeneration of lost supporting tissue. On the tooth side of the element, root membrane cells and blood vessels are allowed to grow into the element from remaining root membrane. On the other side cells of connective tissue (and bone cells) as well as vessels from the connective tissue and bone tissue regions are allowed to grow into the element. It is presumed that the tissue that has grown into the element matures in the manner previously discussed. On the tooth side, root membrane tissue with root cement and root membrane fibers adhering thereto will be formed. On the other side connective tissue and bone will mature.

If the intermediate wall 20 is solid, the coupling between the root membrane and the surrounding tissue will take place mechanically via the double side perforation of the element. When the intermediate wall is perforated, the coupling also will take place directly via the several tissue components from the two sides.

I claim:

1. An element for guided tissue regeneration comprising a slot having a minimum width of 30 micrometers and extending substantially along the surface of the skin by implantation of the element in the intended position thereof, and at least one undercut cavity available from the outside of the element through said slot and extending at either side of the slot, said cavity having a minimum depth of 30 micrometers, the surfaces of the element to be exposed to surrounding tissue comprising a biocompatible material.

2. An element as in claim 1 having several cavities, adjacent cavities being interconnected.

3. An element as in claim 1 wherein the biocompatible material comprises titanium.

4. An element as in claims 1 wherein the biocompatible material comprises vacuum deposited titanium.

5. An element as in claim 1 wherein the cavity is bound by a perforated outer wall.

6. An element as in claim 1 wherein the element is tubular with the cavity available through openings in the outer and inner curved surface of the element.

7. An element as in claim 6 having first cavities which are available through openings in the outer curved surface, and second cavities which are available through openings in the inner curved surface, said first and second cavities being separated by a perforated wall.

8. An element as in claim 1 wherein the element is profiled externally.

* * * * *